United States Patent [19]

Lewis

[11] 4,329,004
[45] May 11, 1982

[54] GAS FILLED HIGH VOLTAGE SLIP RING ASSEMBLY

[75] Inventor: Norris E. Lewis, Christiansburg, Va.

[73] Assignee: Litton Systems, Inc., Blacksburg, Va.

[21] Appl. No.: 148,713

[22] Filed: May 12, 1980

[51] Int. Cl.³ .............................................. H01R 39/00
[52] U.S. Cl. .................................... 339/5 M; 339/5 P
[58] Field of Search ..................................... 339/5, 6, 8

[56] References Cited

U.S. PATENT DOCUMENTS 3,316,519 4/1967 Maytone ................................. 339/5
4,063,792 12/1977 Lodge ................................. 339/5 L Primary Examiner—Joseph H. McGlynn
Assistant Examiner—Frank H. McKenzie, Jr.
Attorney, Agent, or Firm—Brian L. Ribando

[57] ABSTRACT

A slip ring for use in a high voltage system, such as a computerized axial tomography system, including the use of insulating gas, to fill a sealed cavity between a rotor and a stator to maintain the electrical integrity of the slip ring.

2 Claims, 5 Drawing Figures

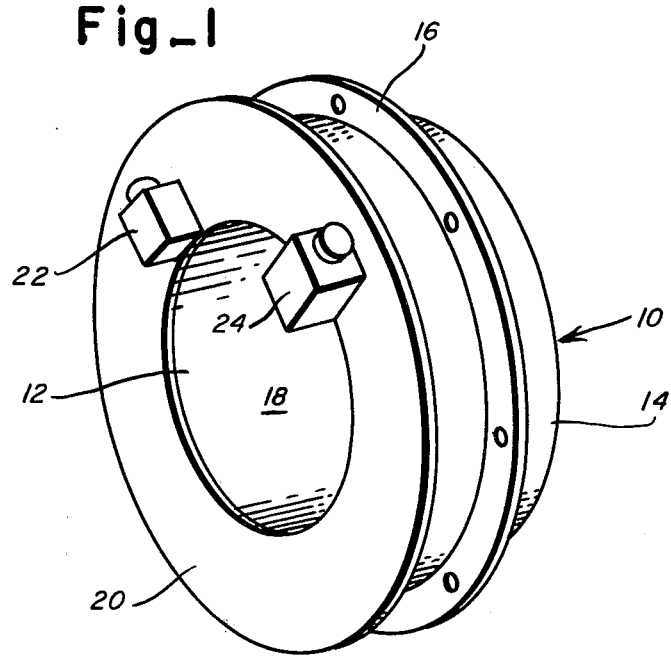
Fig_1
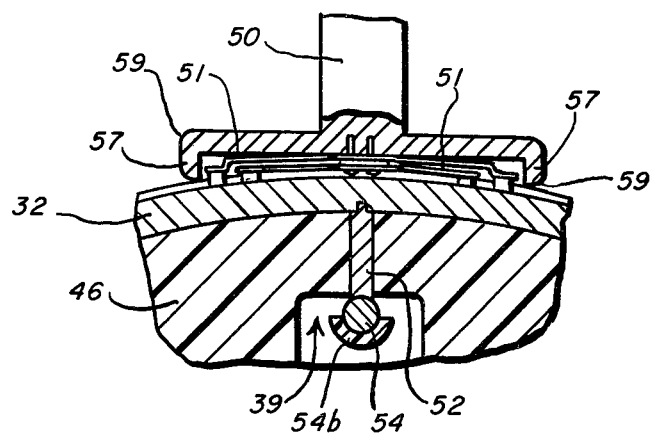
Fig_4

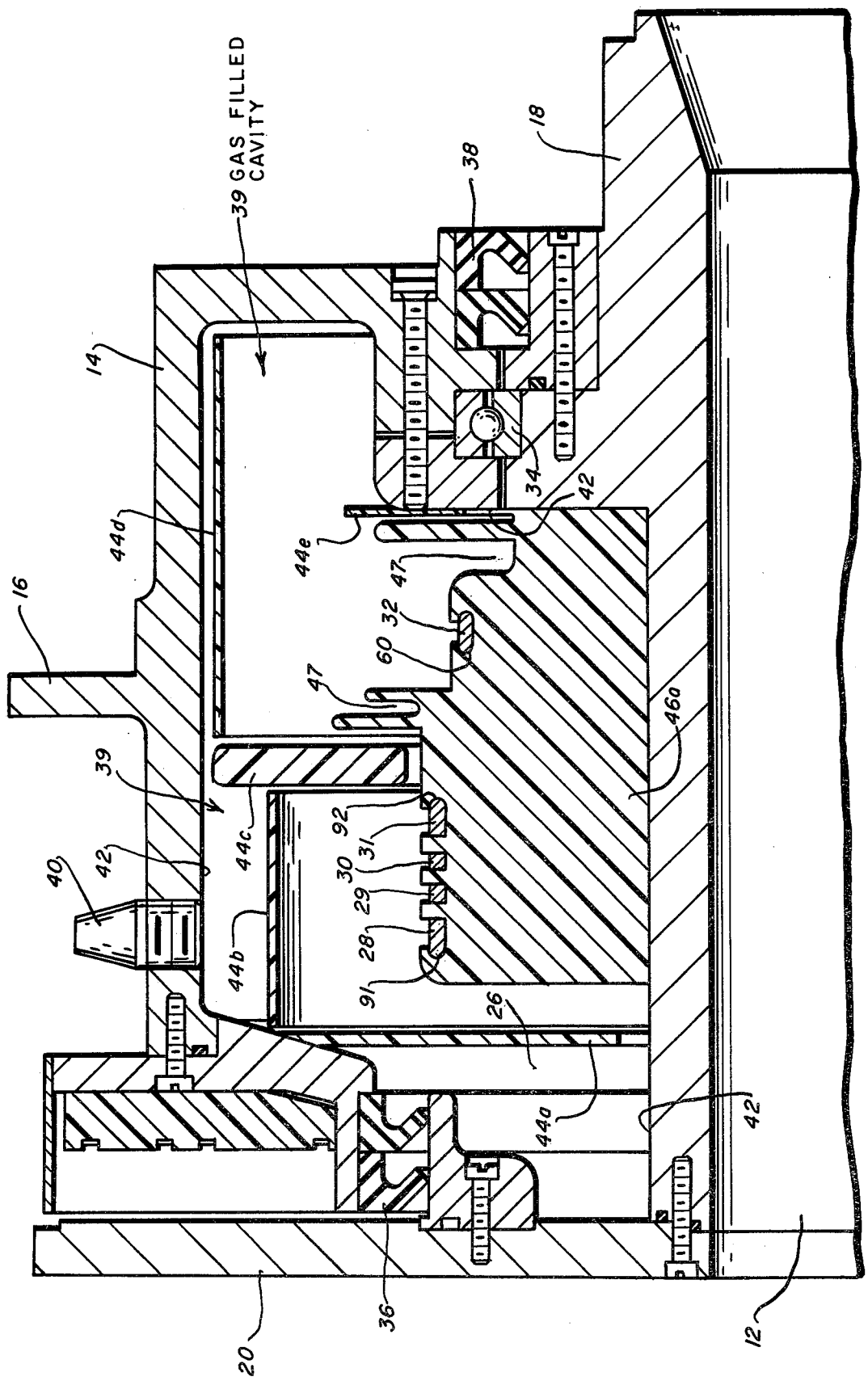
Fig._2

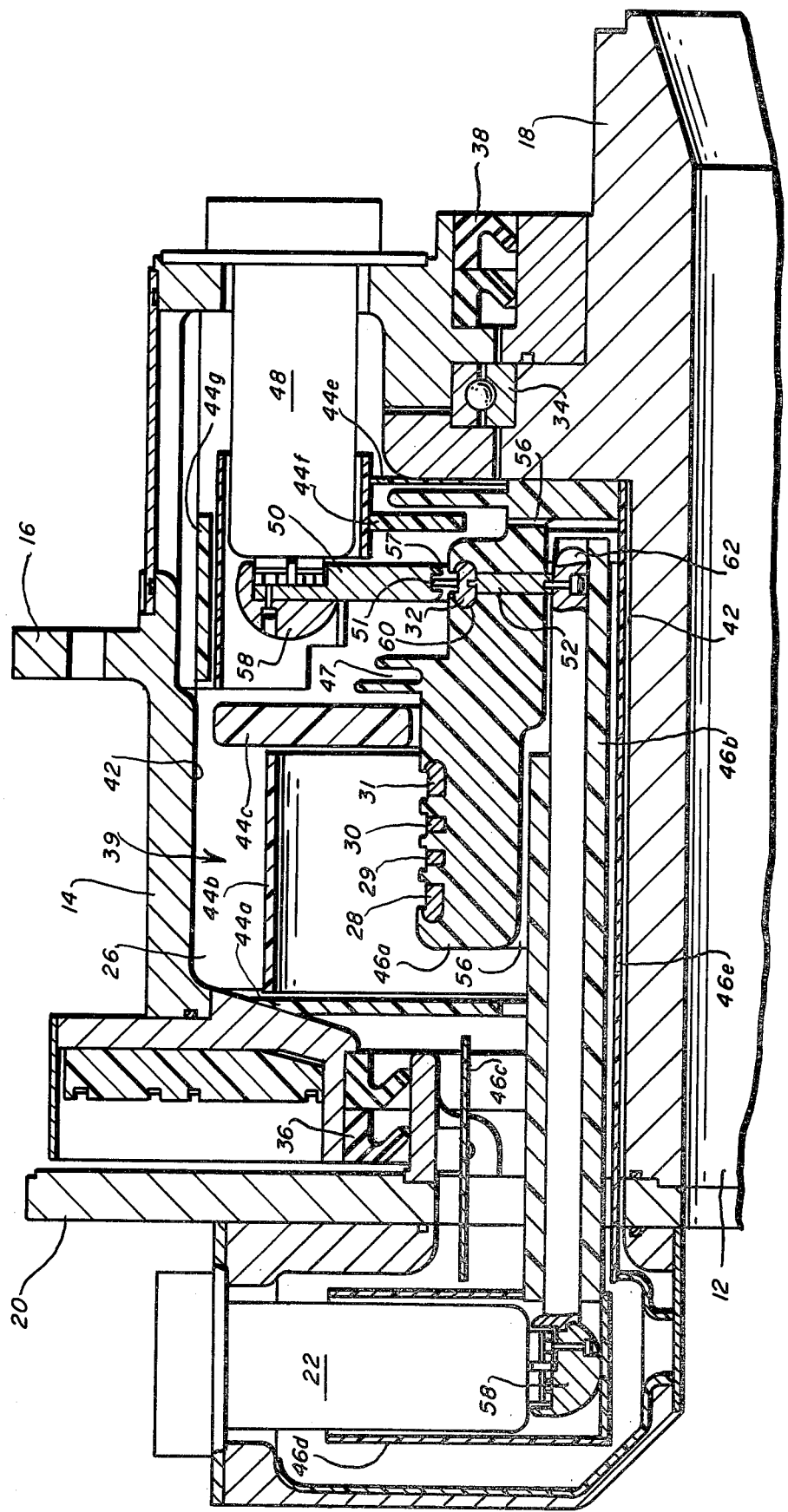
Fig._3

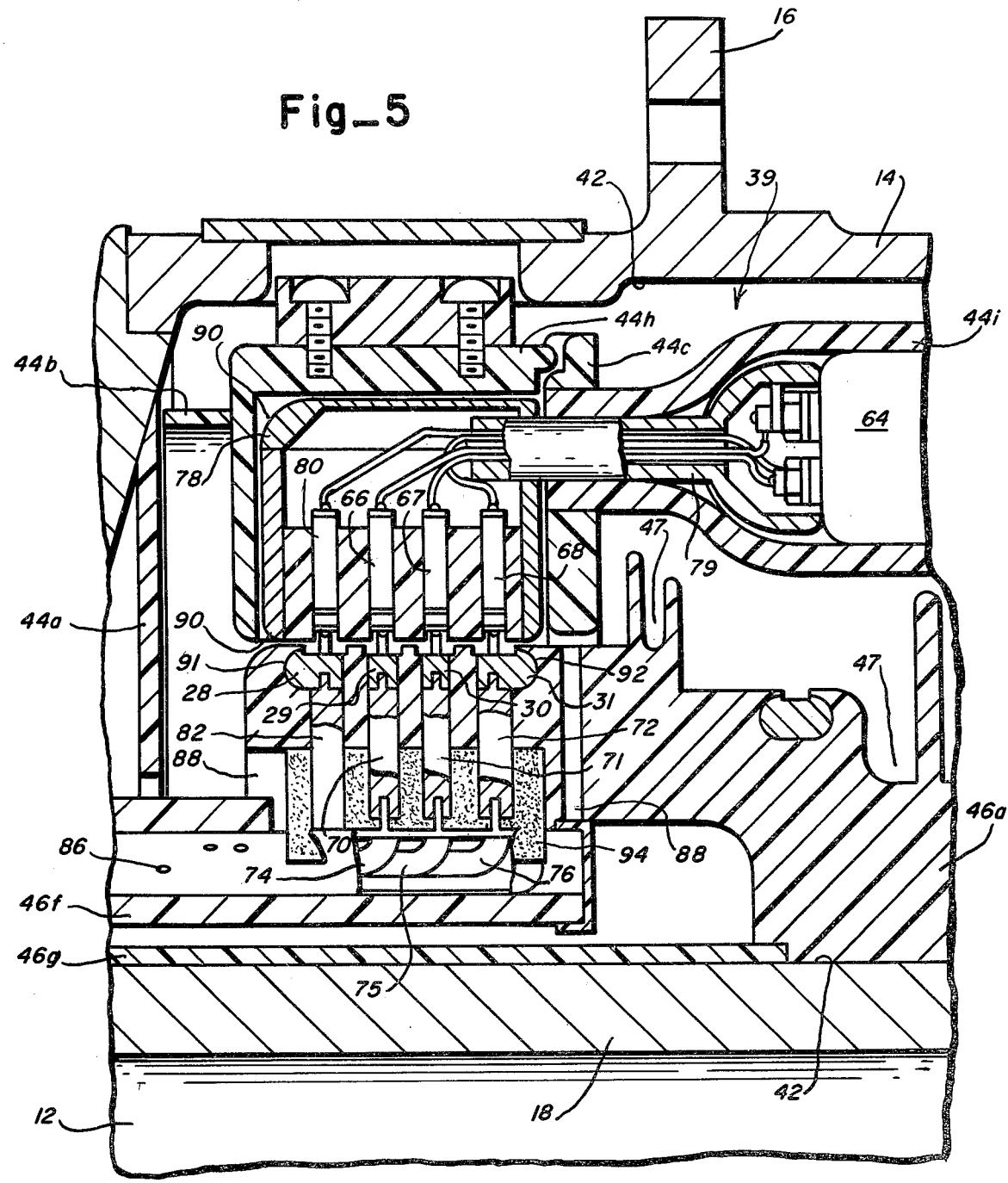
Fig_5

GAS FILLED HIGH VOLTAGE SLIP RING ASSEMBLY

The invention relates to a slip ring assembly for use in a high voltage system, such as a computerized axial tomography system, wherein the slip ring assembly provides the means to transfer power to an orbiting X-ray tube.

In computerized axial tomography scanning systems, an X-ray tube is orbited around a patient and generated data is processed by a computer to yield an X-ray display depicting a desired cross-sectional view of the patient.

The X-ray tube typically requires 150,000 volts in order to operate. This voltage is supplied via a cable connected to the X-ray tube. As the X-ray tube orbits around the body of a patient, the cable winds therearound. The X-ray tube orbiting must, accordingly, be stopped after about one rotation and reversed. It would be highly advantageous to overcome this limitation and be able to orbit an X-ray tube continuously about a patient.

It is, therefore, an object of the invention to provide a slip ring assembly operable at voltages within a 100,000 to 200,000 volt range with a rotational speed up to 200 rpm, and in particular, to provide a slip ring assembly to supply high voltage to an X-ray tube which is used in a computerized axial tomography system.

Additionally, it is an object to provide a high voltage slip ring assembly which utilizes "Freon 12" gas as an electrical insulator.

Other objects and advantages of the present invention will become apparent from the following detailed description of the invention taken in conjunction with the accompanying drawings.

Referring to the drawings:

FIG. 1 is a perspective view of a high voltage slip ring assembly;

FIG. 2 is a sectional view of the top radial portion of the slip ring assembly;

FIGS. 3 is a sectional view of a radial portion of the slip ring assembly showing the anode coupling path in radial alignment.

FIG. 4 is a sectional view of the anode brush block assembly with brushes in contact with the anode ring; and FIG. 5 is a sectional view of a radial portion of the slip ring assembly showing a portion of the cathode coupling path in radial alignment.

As can be seen in FIG. 1, the high voltage slip ring assembly 10 is generally doughnut-shaped having a central bore 12 which is large enough to accommodate an object to be scanned such as a human patient. A stationary cylinder 14, including a mounting ring 16, may be mounted to a suitable support structure (not shown) and provides a means for supporting a rotating structure 18. The rotating structure 18 includes as end mounting plate 20 for supporting an orbiting X-ray tube or other device (not shown) which may be suitably connected to anode and cathode junction boxes 22 and 24 provided thereon. The junction boxes are suitably radially spaced to prevent arcing between the anode and cathode.

Turning now to FIG. 2, it will be seen that the space between the stationary structure or stator 14 and the rotating structure or rotor 18 defines a cavity 26 in which slip rings 28, 29, 30, 31, and 32 are housed. In operation, the anode ring 32 carries a positive potential in the 50–100 KV range. The cathode rings 28, 29, 30 and 31 carry negative potentials in the 50–100 KV range, and the conductive cavity walls 42 remain at ground potential.

The rotor 18 is mounted to the stator 14 on a single bearing ring 34 for rotational movement. Pairs of annular lip-like seals 36 and 38 are used at the interface of the rotor and stator to operatively seal the cavity 26. An inlet with a valve 40 is provided on the top of the assembly for filling the cavity with an insulating gas having a dielectric strength substantially greater than the dielectric strength of air. Various gases are commercially sold as electrical insulators, such as, sulfur hexafluoride ($SF_6$). It was found that dichlorodifluoromethane ($CCL_2F_2$), commonly known as the refrigerant "Freon 12", a trademark, could be utilized as the insulating gas in the slip ring assembly. Due to its widespread availability and its relatively low cost, in the preferred embodiment "Freon 12" gas 39 fills the cavity 26. Other insulating fluids are disclosed in a U.S. patent application filed by the inventor of the instant application and Herbert C. Walker concurrently herewith.

The utilization of "Freon 12" gas in the assembly provides various collateral benefits. If the seals 36 and 38 leak, the gas dissipates in the air instead of causing a possibly hazzardous spill as would be the case if a liquid were used. Since the slip ring assembly may be utilized within a computerized axial tomography system in a hospital setting, this feature is very desirable. Also, the use of a gas, as opposed to a liquid, may be preferred for maintenance purposes.

The "Freon 12" gas 39 permits the assembly to be dimensioned smaller than would be possible if air were used as the dielectric medium in the cavity. Without the gas, short circuiting or arcing would occur during usage.

The use of the insulating gas, however, introduces other problems. The gas contains inherent impurities and other particulate matter which is abraided during operation of the assembly from the brushes, the slip rings, the rubber seals, and the supporting bearings. It is known that these particulates in the gas, responding to the high operational potential differences, create particulate bridges or breakdown paths which cause short circuiting or arcing along sight lines between components which are at different potentials.

In order to prevent the formation of particulate bridges in the slip ring assembly, stationary and rotating dielectric barriers 44a–i and 46a–g, as shown in FIGS. 2, 3, and 5, are mounted within the cavity on the stator and rotor, respectively, blocking all line of sight paths between conductive elements 32, 28–31 and 42 which are at substantially different potentials during operation. The barrier 46a on the rotating structure additionally provides a dielectric mounting base for the slip rings. As can be seen in FIGS. 3 and 5, the barriers 44a–i and 46a–g extend to block line of sight bridging paths in the cavity between the cavity walls 42 and the entire anode and cathode coupling paths.

In the preferred embodiment, the barriers 44a–i and 46a–g are composed of a dielectric material having a dielectric constant which closely matches that of the "Freon 12" gas 39. The matching dielectric properties prevent arcing along the interface of insulating materials 39, 44a–i and 46a–g. Also, selectively grooved portions 47 in the barrier 46a provide a relative long voltage surface creepage path between the cavity wall 42 and the anode ring 32 and between the anode ring 32 and the cathode rings 28-31. Where practical, the barriers are constructed to tightly fit around conductive components, such as where the tubular barrier 46b encases the bus bar 54. This helps to prevent the formation of air pockets within the cavity when it is filled with the "Freon 12" gas.

As can be seen in FIG. 3, the anode coupling path couples a single positive potential from a stationary anode receptacle 48 to the rotating anode junction box 22. A single brush block assembly 50 extends from the anode receptacle 48 and includes four brushes 51 which make sliding electrical contact with the anode slip ring 32 which, in turn, is electrically coupled to the junction box by a cylindrical stud 52 and a cylindrical bus bar 54. Selectively defined apertures 56 in the dielectric barrier 46a allow the insulating gas to surround a portion of the bus bar 54.

In order to reduce the possibility of arcing which is inherent in high voltage systems, Faraday shielding is employed around the brushes 51. As can be seen in FIG. 4, this Faraday shielding comprises the extended portions 57 of the brush block assembly 50 which surrounds the brushes 51 to distribute charge over the shield. Semi-spherical caps 58 which surround the junctions of the anode coupling path with the anode receptacle 48 and junction box 22, the roundness of the stud 52, rounded brush block assembly portions 59, rounded ring edges 60, and roundness of bus bar 54 including rounded end 62 additionally help to prevent charge build-up which would otherwise occur at sharp corners and which would be prime sources of unwanted arcing.

As can be seen in FIG. 5, the cathode coupling path couples a plurality of negative potentials from a stationary cathode receptacle 64 to the cathode junction box 24. Four brush assemblies 66, 67, 68 and 80, including leads extending from the cathode receptacle 64, are in sliding electrical contact with respective slip rings 29, 30, 31 and 28. The four brush assemblies 66, 67, 68 and 80 are encased in a housing 78 and a cylindrical member 79 which are electrically coupled to the fourth brush assembly 80 to provide Faraday shielding for the entire cathode brush block. The barrier 44h extends to surround the Faraday shield housing 78. Three of the rings 29, 30 and 31 are coupled to the junction box 24 by connecting studs 70, 71 and 72 and a cable 74, 75 and 76, respectively. The fourth ring 28 is coupled by a connecting stud 82 to a tube 84 surrounding the cathode cables 74, 75 and 76 which, in turn, is connected to the cathode junction box 24. The tube serves both as a conductive circuit element and as a Faraday shield for the cables 74, 75 and 76. Both the tube 84 and the dielectric barrier 46a contain apertures 86 and 88 to allow the gas to surround the cables 74, 75 and 76.

Rounded exterior corners and edges of the Faraday shield housing 90, roundness of the connecting studs 70, 71, 72 and 82, a rounded outside edge 91 and 92 on each of the end rings 28 and 31, and the relatively large radii of both the cylindrical member 79 and the tube 84 help to reduce the possibility of arcing along the cathode coupling path through charge distribution. The studs 70, 71, 72 and 82, which are not fully shielded, are partially encased in a semi-conductive material 94 which, similar to a Faraday shield, prevents arcing by preventing charge build-up. The semi-conductive material 94 conducts sufficiently to distribute charges over its relatively large surface area while permitting the various negative potentials carried by the studs to remain distinct. Without the semi-conductive material 94, charge build-up could occur at the narrow junctions between the studs 70, 71 and 72 and cables 74, 75 and 76 which could cause arcing.

Any number of circuits could be coupled using the principles embodied in the construction of the cathode coupling path as shown in FIG. 5. However, if only a single negative potential were to be coupled, the cathode coupling path could be structured similar to the anode path without the semi-conductive material.

What is claimed is:
1. A high voltage slip ring assembly comprising:
   a rotor and a stator for defining a cavity therebetween
   an insulating gas having a dielectric strength substantially greater than the dielectric strength of air filling said cavity,
   seal means operatively sealing said cavity for retaining said gas therein,
   at least one electrical coupling means within said cavity for coupling power from the stator to the rotor,
   whereby operational short circuiting and arcing within said cavity is prevented.
2. A high voltage slip ring assembly according to claim 1, wherein the insulating gas is comprised of dichlorodifluoromethane.

* * * * *